United States Patent [19]

Pinsukanjana et al.

[11] Patent Number: 6,075,588

[45] Date of Patent: Jun. 13, 2000

[54] INTEGRATED MULTI-CHANNEL OPTICAL-BASED FLUX MONITOR AND METHOD

[75] Inventors: Paul Ruengrit Pinsukanjana; Arthur Charles Gossard; Andrew William Jackson, all of Santa Barbara; Jan Arild Tofte, Goleta; Scott Arlen Chalmers, San Diego, all of Calif.

[73] Assignee: The Regents of the University of California, Oakland, Calif.

[21] Appl. No.: 08/657,614

[22] Filed: May 31, 1996

[51] Int. Cl.[7] .................................................... G01J 3/42
[52] U.S. Cl. ............................................ 356/72; 356/325
[58] Field of Search ............................... 356/72, 319, 323, 356/325; 250/339.07, 337.11, 341.8, 227.18, 227.23

[56] References Cited

U.S. PATENT DOCUMENTS

| | | | |
|---|---|---|---|
| 3,865,625 | 2/1975 | Cho et al. . | |
| 4,300,833 | 11/1981 | Harnly et al. | 356/307 |
| 4,815,848 | 3/1989 | Hadeishi | 356/320 |
| 4,945,254 | 7/1990 | Robbins | 356/445 |
| 5,038,038 | 8/1991 | Weniger et al. | 250/341.8 X |
| 5,066,124 | 11/1991 | Wulf | 356/312 |
| 5,171,399 | 12/1992 | Brennan et al. | 156/601 |
| 5,254,207 | 10/1993 | Nishizawa et al. | 356/318 X |
| 5,364,492 | 11/1994 | Eckstein et al. | 356/309 X |
| 5,399,521 | 3/1995 | Celii et al. | 437/105 |
| 5,400,739 | 3/1995 | Kao et al. | 437/105 X |

OTHER PUBLICATIONS

Feher et al. "Tunable Diode Laser Monitoring of Atmospheric Trace Gas Constituents" Spectrochimica Acta Part A 51 (1995), pp. 1579 and 1590. Only p. 1590 Used in Rejection 1995.

Fried et al "Versatile Integrated Tunable Diode Laser System for High Precision: Application for Ambient Measurements of OCS" Applied Optics vol. 30#15/May 20, 1991, pp. 1916–1920.

Ahearn "Optical Bridge for an Atomic Absorption Rate Monitor and Control System" IBM Tech. Disc. Bulletin, vol. 14 #June 1, 1971 pp. 148–149.

T.Y. Kometani and W. Wiegmann, "Measurements of Ga and Al in a Molecular–beam Epitaxy Chamber by Atomic Absorption Spectrometry (AAS)," *J. Vac. Sci. Technol.*, vol. 12, No. 4, Jul./Aug. 1995, 933–936.

M.E. Klausmeier–Brown, J.E. Eckstein, I. Bozovic, and G.F. Virshup, "Accurate Measurement of Atomic Beam Flux by Pseudo–double–beam Atomic Absorption Spectroscopy for Growth of Thin–film Oxide Superconductors," *Appl. Phys. Lett.*, vol. 60, No. 5, Feb. 3, 1992, 657–659.

S.A. Chalmers and K.P. Killeen, "Real–time Control of Molecular Beam Epitaxy by Optical–based Flux Monitoring," *Appl. Phys. Lett.*, vol. 63, No. 23, Dec. 6, 1993, 3131–3133.

S.A. Chalmers, K.P. Killeen and E.D. Jones, "Accurate Multiple–quantum–well Growth Using Real–time Optical Flux Monitoring," *Appl. Phys. Lett.*, vol. 65, No. 1, Jul. 4, 1994, 4–6.

S.J. Benerofe, C.H. Ahn, M.M. Wang K.E. Kihlstrom, K.B. Do, S.B. Arnason, M.M. Fejer, T.H. Geballe, M.R. Beasley and R.H. Hammond "Dual Beam Atomic Absorption Spectroscopy for Controlling Thin Film Deposition Rates," *J. Vac. Sci. Technol. B*, vol. 12, No. 2, Mar./Apr. 1994, 1217–1220.

(List continued on next page.)

*Primary Examiner*—F. L. Evans
*Attorney, Agent, or Firm*—Merchant, Gould, Smith, Edell, Welter & Schmidt

[57] ABSTRACT

An integrated dual beam multi-channel optical-based flux monitor and method of monitoring atomic absorption of a plurality of atomic species during epitaxial growth. Light from multiple sources is simultaneously passed through a region of deposition of material such that atomic absorption takes place. The light that passed through the region is then compared to light in a reference arm that did not pass through a region of atomic absorption. From this comparison the growth of an epitaxial layer can be carefully controlled.

58 Claims, 10 Drawing Sheets

OTHER PUBLICATIONS

C. Lu and Y. Guan, "Improved Method of Nonintrusive Deposition Rate Monitoring by Atomic Absorption Spectroscopy for Physical Vapor Deposition Processes," *J. Vac. Sci. Technol. A,* vol. 13, No. 3, May/Jun. 1995, 1797–1801.

Brochure, "Atomicas A New Breakthrough in Thin Film Deposition Rate Monitoring technology," Intelligent Sensor Technology, Inc., Mountain View, CA, Oct. 1994, 4 pages.

Weizhi Wang, R. H. Hammond, M. M. Fejer, C. H. Ahn and M.R. Beasley; M.D. Levenson and M. L. Bortz, "Diode–Laser–Based Atomic Absorption Monitor Using Frequency–Modulation Spectroscopy for Physical Vapor Deposition Process Control," *App. Phys. Lett.,* vol. 67, No. 10, Sep. 4, 1995, pp. 1375–1377.

Weizhi Wang, M. M. Feher, R. H. Hammond, M. R. Beasley, and C. H. Ahn; M. L. Bortz and T. Day, "Atomic Absorption Monitor for Deposition Process Control of Aluminum at 394 nm Using Frequency–Doubled Diode Laser," *Appl. Phys. Lett.,* vol. 68, No. 5, Feb. 5, 1996, pp. 729–731.

R. Fischer, J. Klem, T. J. Drummond, R. E. Thorne, W. Kopp, H. Morkoc and A. Y. Cho, "Incorporation Rates of Gallium and Aluminum on GaAs During Molecular Beam Epitaxy at High Substrate Temperatures," *J. of Appl. Phys.,* vol. 54, No. 5, pp. 2508–2510, May 1983.

F. G. Celii, Y.–C. Kao, A. J. Katz, and T. S. Moise, "Real–time Monitoring of Resonant–tunneling Diode Growth Using Spectroscopic Ellipsometry," *J. Vac. Sci. Technol. A,* vol. 13, No. 3, pp. 733–739, May/Jun. 1995.

Jan P.A. van der Wagt and J. S. Harris, Jr., Reflection High–energy Electron Diffraction Intensity Oscillations During Molecular–Beam Epitaxy on Rotating Substrates, *J. Vac. Sci. Technol. B,* vol. 12, No. 2, pp. 1236–1237, Mar./Apr. 1993.

INTEGRATED MULTI-CHANNEL OPTICAL-BASED FLUX MONITOR AND METHOD

STATEMENT AS TO RIGHTS TO INVENTIONS MADE UNDER FEDERALLY SPONSORED RESEARCH AND DEVELOPMENT

This invention was made with Government support under Grant/Contract Nos. DMR-9120007, MDA 972-94-10002, DAAH 0493-G-1256, awarded by the National Science Foundation and the Army. The Government has certain rights in this invention.

BACKGROUND OF THE INVENTION

1. Field of the Invention

The present invention involves the monitoring of growth rate and composition of an epitaxial layer being fabricated from a plurality of atomic species in a vacuum chamber.

Many widely known deposition techniques such as molecular beam epitaxy (MBE) and electron-beam evaporation are used in the fabrication of many types of devices including electronic and opto-electronic devices. An important need exists to improve both the accuracy and the yield of high performance electronic and opto-electronic device fabrication. Some examples of these devices are Resonant Tunnel Diodes (RTD), Vertical Cavity Surface Emitting Lasers (VCSEL), electro-optical modulators, and quantum well lasers. Often, the process for making these device involves growing thousands of distinct epitaxial layers while maintaining strict control of the composition and thickness of each layer. In addition, there are further constraints such as:

1) limited access of the monitoring system to the vacuum growth chamber.
2) monitoring system has to be non-invasive to the growth process.
3) error due to noise and drift has to be sufficiently small during the course of the growth.
4) monitoring system must have a high rejection of stray light from the surrounding environment.
5) monitoring system must not be affected by special requirements such as sample rotation during MBE growth.
6) the monitoring system should be portable and most of the setup should be remote from the growth chamber.

Currently, many epitaxial deposition techniques such as electron-beam evaporation and Molecular Beam Epitaxy (MBE) lack good growth monitoring systems which have the ability to monitor in real-time the growth rate as well as composition during multi-component epitaxial growth. Included among these monitoring systems is the technique of atomic absorption.

It has long been recognized that atomic absorption can be used as a tool for monitoring and control of material deposition processes. Atomic absorption techniques generally involve passing a light beam through the molecular beam of the MBE process and then measuring the resulting intensity of the light beam. The more atoms that are being deposited, the greater the atomic absorption, resulting in a lower intensity of light. The light beam must have a wavelength that corresponds with the atomic species desired to be measured. In this way the growth of the epitaxial layers with respect to a particular atomic species can be measured. Recently, because of a need for better non-invasive real-time feedback during the growth process, increased attention has been turned toward monitoring techniques using atomic absorption of the molecular beam flux.

2. Description of the Related Art

There have been many prior monitoring systems which utilize the atomic absorption technique. However, the prior art discloses the monitoring of just one channel at a time with the possibility of combining several independent one-channel units to build a multi-channel system. These multi-channel systems do not integrate the channels and therefore require additional port space in the vacuum chamber.

Appl. Phys. Lett. 60 (5) Feb. 3, 1992, p. 657, (Klausmeier et al.), discloses the passing of a modulated light beam through the molecular beam of an MBE process and then passing the light beam through a bandpass filter and into a photomultiplier tube. The filter passes only a particular emission line so that only the growth of the atomic beam flux corresponding to that particular wavelength is measured. If more than one atomic beam flux is being deposited on the substrate then the Klausmeier device can only measure the growth rate and composition of one atomic species.

J.Vac.Sci.Technol.B 12(2), March/April 1994, p. 217, and J. Vac. Sci. Technol. A 13(3), May/June 1995, p. 1797, disclose a system similar to Klausmeier's and the implementation of multiple channels is not directly addressed.

Appl. Phys. Lett. 63 (23), Dec. 6, 1993, p. 3131, and Appl. Phys. Lett. 65 (1), Jul. 4, 1994, p. 4, disclose a dual-beam configuration with two channels but it is not optimized for the limited optical access that exists in most MBE and electron beam evaporation systems. The two channels are not integrated to follow one path through the molecular beam and therefore require more port space to the vacuum chamber.

SUMMARY OF INVENTION

It is an object of the present invention to present a novel apparatus for measuring growth rate and composition of an epitaxial layer, during growth, by monitoring the atomic absorption of several atomic beam fluxes simultaneously.

It is a further object of the invention to provide a method for monitoring the growth of several atomic species simultaneously via utilization of atomic absorption.

The present invention is optimized for low absorption level and integrated multi-channel atomic absorption monitoring using fiber optics. The invention includes an integrated multi-channel optical monitoring system which simultaneously monitors the atomic absorption of distinct atomic species during epitaxial growth. The concept of atomic absorption is that when light of a particular wavelength passes through an atomic species which absorbs light of the same wavelength then some of the light is absorbed by the atomic species. Therefore, one light source is needed for each atomic species desired to be measured. In a preferred embodiment, the light source corresponding to each atomic species is atomic emission radiation from a hollow cathode lamp. There are at least two embodiments of the present invention. In both embodiments, the beams from the different wavelengths overlap inside of the vacuum chamber and are discriminated by different chopping frequencies. Under limited optical access, therefore, it is still possible to probe the atomic absorption of several atomic species simultaneously. In both embodiments, only one pair of through optical ports or one optical port with a set of mirrors is used in the vacuum chamber.

In a first embodiment, the light from each of the light sources is modulated at a distinct frequency by a mechanical chopper and then combined into one beam through a combining optical fiber bundle. The combined beam is divided into a reference arm and a signal arm and then collected by two optical fibers. The reference arm is used to compensate for lamp intensity drift. The light in the signal arm is sent through the region within the vacuum chamber through which the flux of material being deposited is passing. The signals are detected with two detectors. The modulated signals are recovered using lock-in amplifiers. This configuration is useful when optical access to the region is limited.

In a second embodiment, the light of each channel is kept separated and individually divided into the reference and the signal arms. The light in the reference arms and signal arms of all channels are chopped at different chopping frequencies. The light in the signal arm is sent through the region and then collected by another set of optical fibers. For each channel, the light in the signal arm and the light in the reference arm is then combined and detected with the same detector.

An advantage of the second embodiment is that the light from the signal and the reference arms for each atomic line are monitored by the same detector. Drift of these light beams with respect to each other due to the detector is virtually eliminated.

BRIEF DESCRIPTION OF THE DRAWINGS

Referring now to the drawings in which like reference numbers represent corresponding parts throughout:

FIG. 11 is a graph showing the atomic absorption signals as a function of growth rate for Ga and In.

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Figure 1:
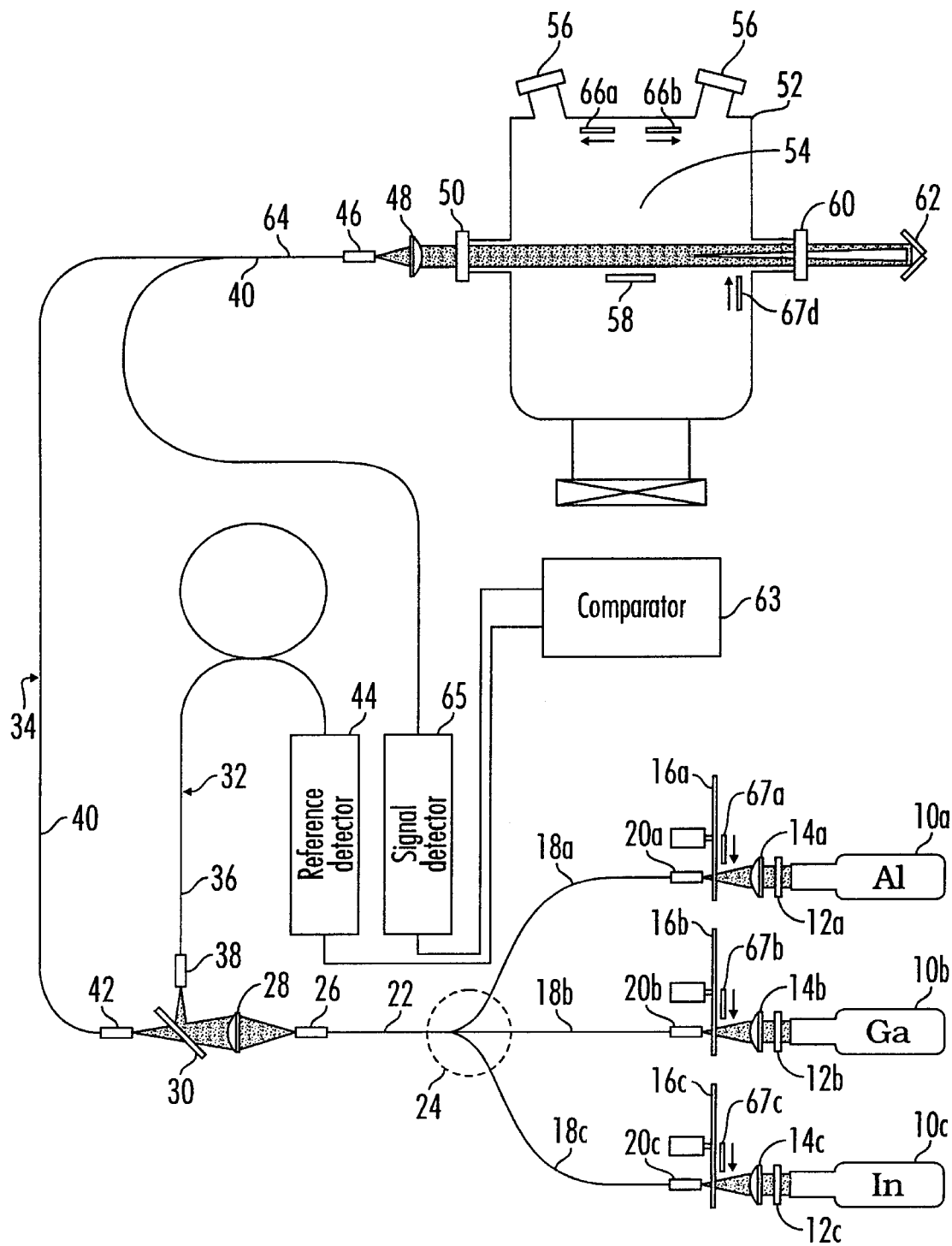
FIG. 1 is a schematic diagram of the first embodiment of the invention.
Figure 4:
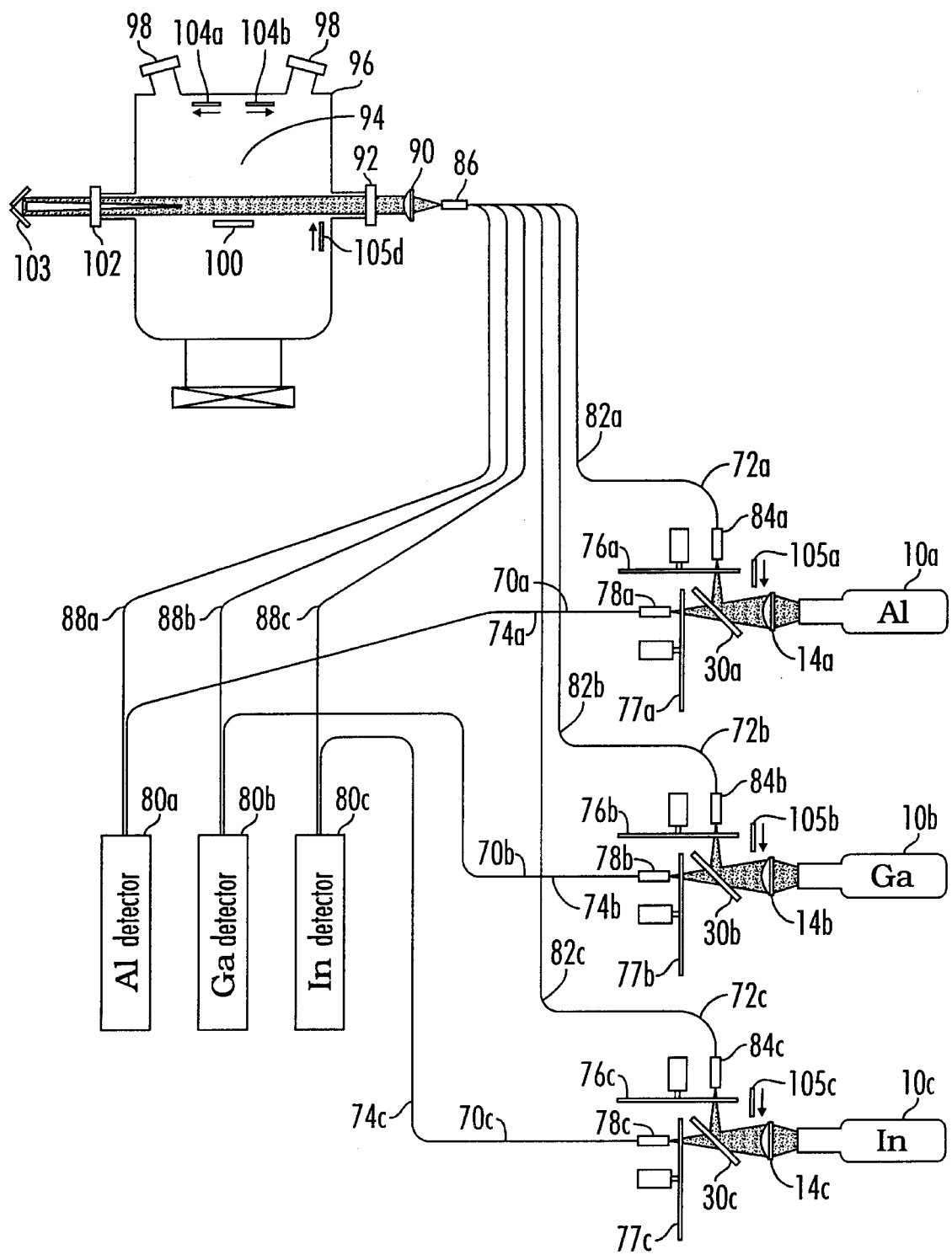
FIG. 4 is a schematic diagram of the second embodiment of the invention.

The schematic diagrams for two versions of the invention are shown in FIGS. 1 and 4, respectively. These FIGS. are specific to a three-channel optical based flux monitor (OFM) which monitors Al, Ga, and In simultaneously. The same principle may also be applied to a monitoring system with more or fewer channels and with other elements. Because each growth system is unique, different optimization criteria have to be considered for each specific application. The description below is optimized for a solid source GEN II MBE system configured for III–V semiconductor material system, i.e., AlGaInAs. The typical growth rates are in the range of $10^{-1}$ to $10^0$ monolayers per second. The devices are grown under As over-pressure and with unity sticking coefficient for the group III elements. However, one skilled in the art would recognize how to correct for non-unity sticking coefficient.

In the first embodiment, as shown in FIG. 1, the light sources 10a–c are hollow cathode lamps (HCL). Alternatively, the light sources 10a–c can be laser diodes or laser systems. Light source 10a is an Aluminum (Al) source and therefore it emits light with frequencies corresponding to Aluminum. Light sources 10b and 10c are Gallium (Ga) and Indium (In) sources, respectively. The HCL's can be operated under constant current or under constant light output mode. The light from the light sources 10a–c is filtered by narrow bandpass filters 12a–c, respectively, resulting in a bandpass output corresponding to each light source. Typically, for Al, Ga, and In, the narrow bandpass region is centered at corresponding emission lines which are at 395 nm, 417 nm, and 410 nm respectively with a typical bandwidth of 10 nm. Each bandpass output travels through a lens 14a–c respectively, which focuses the light. Each bandpass output is modulated by a mechanical chopper 16a–c such that each chopper has a frequency different than the other two. By modulating the light, the system is less sensitive to the negative effects of stray light and the different channels can be demultiplexed. The bandpass outputs then enter optic fibers 18a–c respectively, through fiber input ends 20a–c, respectively. As can be seen by FIG. 1 each of the three bandpass outputs enter into a separate optic fiber designated as 18a–c, respectively. The three bandpass outputs are then combined into a combined beam in one optic fiber 22 using a trifurcating optical fiber bundle 24. A trifurcating optical fiber bundle has three optic fibers as inputs and one optic fiber as an output. The three bandpass outputs in the optic fibers 18a–c are combined into one combined beam in one optic fiber 22. The combining means does not have to be a trifurcating optical fiber bundle. If, for example, only two light sources are used then the combining means would combine the two bandpass outputs into one combined beam. The combined beam exits the optic fiber 22 through fiber output end 26 and then the combined beam goes through lens 28. The combined beam is then split by a beam splitter 30 into two arms. One arm is the reference arm 32; the other, the signal arm 34. The light split into the reference arm 32 is collected by optic fiber 36, with fiber input end 38. The light split into the signal arm 34 is collected by optic fiber 40, with fiber input end 42. The optic fibers 36 and 40 are multi-mode and have a 1 mm core diameter with numerical aperture (NA)=0.16.

The reference arm 32 (which is what makes this a dual beam system) is used to compensate for drifts in light source intensity. The three bandpass outputs in the combined beam of the reference arm 32 are detected by the detector 44. In the preferred embodiment the detector 44 comprises a collimating lens, filter, photomultiplier tube (PMT) and three phase sensitive lock-in amplifiers. The PMT measures the intensity of the bandpass outputs. The phase sensitive lock-in amplifiers are used to demultiplex the modulated bandpass outputs measured by the PMT. The detector 44 produces a plurality of reference signals, each reference signal corresponding to the intensity of a demultiplexed bandpass output. In the preferred embodiment as described here, the plurality of reference signals would be three reference signals corresponding to the three bandpass outputs. If, for example, four atomic species were to be detected, then four light sources and four phase sensitive lock-in amplifiers would be used.

The combined beam in the signal arm 34 travels in optic fiber 40 and exits the optic fiber 40 through fiber output end 46. The combined beam in the signal arm then travels through collimating lens 48 and through the first port 50 of vacuum chamber 52. The combined beam of the signal arm 34 is then sent through the vacuum chamber 52, passing through a region 54 between the sources 56 and the substrate 58. The combined beam of the signal arm 34 then exits the vacuum chamber 52 through a second port 60 and is retroreflected by retroreflector 62 back into the vacuum chamber 52 via the second port 60. The optical ports on the MBE system of a preferred embodiment are 5 degree glancing-angle optical ports, 1.51" in diameter and approximately 3 feet apart. The retroreflector 62 comprises two mirrors situated such that the light reflected by the retroreflector 62 is returned along substantially the same path, but in the opposite direction, as the incoming light. The light from the signal arm 34 does not strike the substrate 58. The combined beam of the signal arm 34 then exits the vacuum chamber 52 through the first port 50. The combined beam of the signal arm 34, therefore, passes through the region 54 two times. It is within the scope of the present invention to have only a single pass through the region 54, in which case the atomic absorption would be reduced. The double pass through the region 54 increases the absorption level. If the vacuum chamber had more optical access, i.e., larger optical ports or shorter optical travel distance, multi-pass of the light in the signal arm through the region 54 could be implemented. This would increase the absorption level and might make monitoring of a much weaker absorption signal possible.

Because the returning beam—after bouncing through the two mirrors of the retroreflector 62—nearly retraces the optical path of the incident beam, it is refocused to a spot approximately the same spot size as the core diameter of the optic fiber 34. To increase light collection efficiency, the returning spot is focused onto a larger 1.5 mm core diameter collection optical fiber 64 with NA=0.39. The collection fiber 64 and the optic fiber 40 are within the same casing and therefore cannot be separately seen in FIG. 1. The collection fiber 64 then carries the combined light of the signal arm 34 to the detector 65. The detector 65 is the same as detector 44, except that the output of detector 65 is a probe signal and it is proportional to the intensity of the light received by the detector. While the remoteness of the monitoring system (detectors, etc.) made possible by the optic fibers is a desired characteristic, an alternative embodiment of the present invention could be implemented in which the detector 65 could be mounted on the port opposite the injection side (second port 60).

The reference signals and the probe signals are input to the comparator 63 that completes the comparison of the light in the signal arm 34 to the light in the reference arm 32 returning the atomic absorption level according to the normalization and calibration formulas described below. The comparator 63 is implemented in either hardware or software as is well known in the art.

The molecular beam shutters 66a–b and optical shutters 67a–d are used in conjunction with the normalization and calibration of the setup which is discussed below. The molecular beam shutters 66a–b block the flux of material from striking the substrate when closed. The optical shutters 67a–d block light from passing therethrough. The position of the shutters shown in the drawings is not meant to be limiting and one skilled in the art will realize that there are numerous locations in which these shutters can be placed and still block the light. The molecular beam shutters 66a–b and the optical shutters 67a–d can be made of any material that substantially blocks the passage of light. For example, a piece of cardboard can be used.

Figure 2:
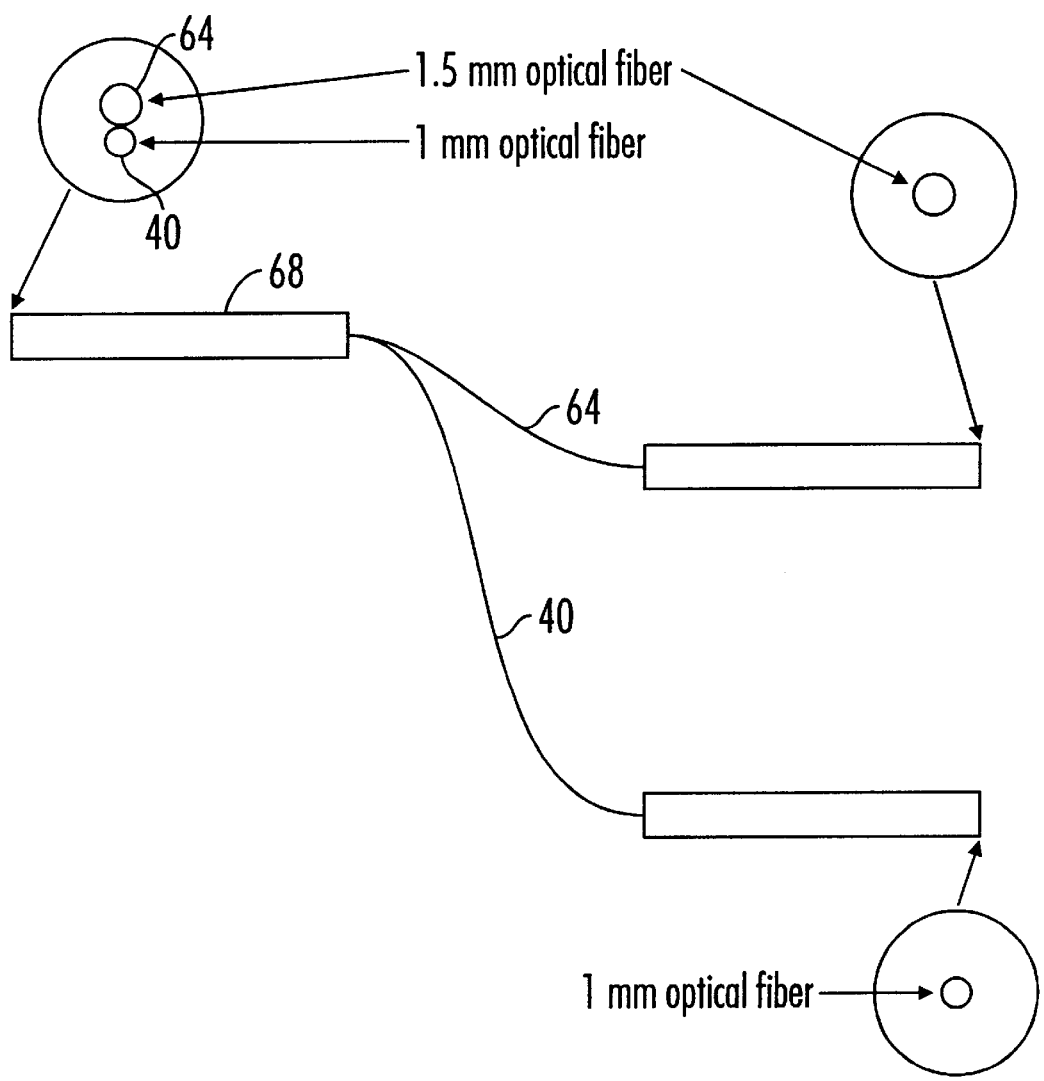
FIG. 2 is a view of the fiber optics in the first embodiment.

FIG. 2 is a view of the fiber optics in the first embodiment. The combined beam enters the vacuum chamber from optic fiber 40 (1 mm) and after making two passes through the region 54 is collected in collection fiber 64 (1.5 mm) to be delivered to the detector 65. As can be seen in both FIGS. 1 and 2, the optic fiber 40 and collection fiber 64 are adjacent to one another (in the same housing 68) near the injection and collection area.

Figure 3:
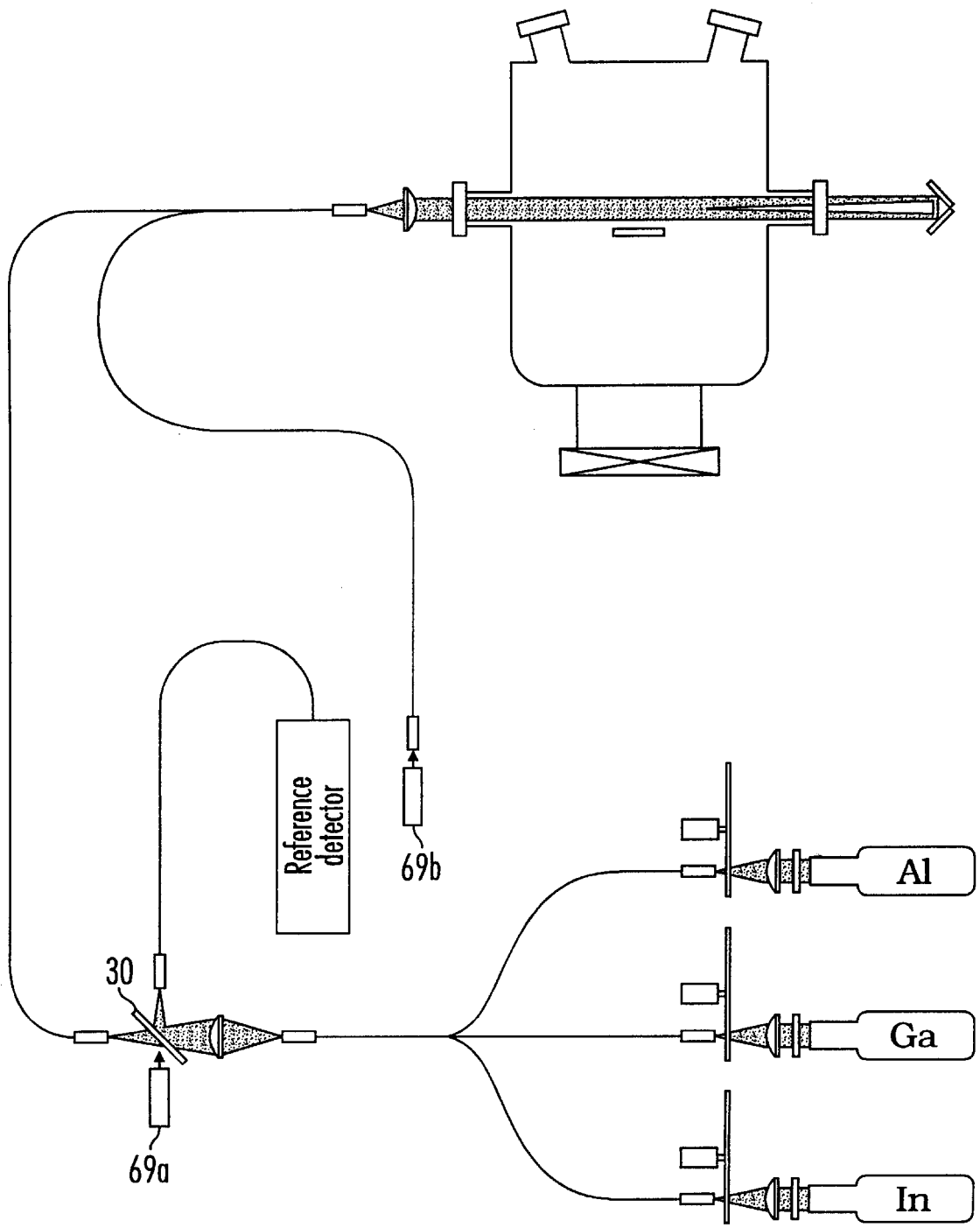
FIG. 3 is a schematic diagram of the first embodiment including the alignment light source.

FIG. 3 is a schematic diagram of the first embodiment including the alignment light source 69. The purpose of an alignment light source is to make alignment of the optical path through the vacuum chamber simpler by providing a brighter visual indication of the path of the light. The alignment light source 69 is injected through one of the arms of the beam splitter 30 as shown in FIG. 3. The other alignment light source replaces the detector 65 during alignment. Once properly aligned, the detector 65 can be re-connected back to the fiber optic network. Note that the optical alignment from a fiber end to a detector is generally not very critical.

In order to make the alignment of the optical path through the vacuum chamber 52 simpler, brighter light sources such as commercially available (red) diode lasers or high brightness blue LED's can be easily integrated into the optical setup without sacrificing system performance. Other possibilities for bright light sources are other types of lasers or lamps. Diode lasers and/or LED's are preferred because they are compact, economical, and easy to use.

Another advantage of diode lasers are that the optical beam is collimated. Because the wavelength of a blue LED (450 nm) is much closer to the monitored wavelength of Al, Ga, and In (at 395, 417 and 410 nm respectively) than a red laser diode (670 nm), the optical beam profile of blue LED's through the fiber optic network will be more similar to those of the monitored wavelengths. On the down side, LED's are not as bright as diode lasers.

Based on experimental tests of the first embodiment, the long term drifts of the ratio signal—intensity of the light in the collection fiber 64 divided by the intensity of the light in the reference arm 32—is within 1 part in 1000 per hour over the course of a day.

FIG. 4 is a schematic diagram of the second embodiment of the invention. In the second embodiment the optical beam of each channel is kept separated from the optical beam of another channel until they are positionally and angularly multiplexed (integrated) to pass through the vacuum chamber together. The light sources are positionally and angularly multiplexed by placing the optic fibers 82a–c substantially adjacent to one another. The light sources 10a–c which can be hollow cathode lamps, laser diodes, laser systems or any other type of source of light, emit light which travels through lenses 14a–c and is then split by beam splitters 30a–c into reference arms 70a–c and signal arms 72a–c. The light in each of the signal arms 72a–c and the reference arms 70a–c is modulated with mechanical choppers 76a–c and 77a–c, respectively. There are a total of six choppers, all chopping at different frequencies, one for each of the reference arms 70a–c and one for each of the signal arms 72a–c for each of the light sources 10a–c.

After the light in the reference arms 70a–c has been modulated, it enters optic fibers 74a–c via the fiber input ends 78a–c. The optic fibers 74a–c carry the light to the respective detectors 80a–c.

The light in the signal arms 72a–c enters the respective optic fibers 82a–c, via the fiber input ends 84a–c. The three optic fibers 82a–c are adjacent to one another near the fiber output end 86 so that the light emitted is positionally and angularly multiplexed. In other words, the three light beams that exit the optic fibers 82a–c have paths that are substantially parallel to each other and the light beams overlap due to the fact that the light beams originate from different yet adjacent positions. Additionally, there are three collection optic fibers 88a–c which are linearly adjacent to the three optic fibers 82a–c. The light in the signal arms 72a–c exits the optic fibers 82a–c via the fiber output end 86 and passes through a common collimating lens 90, through a first port 92, and through a region 94 in the vacuum chamber 96 which is between the sources 98 and the substrate 100. The flux of material being deposited onto the substrate 100 flows from the sources 98, through the region 94 and onto the substrate 100. Therefore, the positionally and angularly multiplexed light from the signal arms 72a–c passes through the flux of material being deposited onto the substrate 100. The light from the signal arms 72a–c does not strike the substrate 100. The light from the signal arms 72a–c exits the vacuum chamber 96 at a second port 102 and is retroreflected by retroreflector 103, nearly retracing the original optical path through the region 94. The light exits the vacuum chamber 96 through the first port and through the lens 90 which refocuses the light into three separate locations. Because the light is positionally and angularly multiplexed the refocused light enters the collection fibers 88a–c such that the light that exited optic fibers 82a–c enters collection fibers 88a–c respectively.

The light in the collection fibers 88a–c is then received by the detectors 80a–c respectively. Because the light in the signal arms 72a–c is modulated at a different frequency than the light in the reference arms 70a–c, the detectors 80a–c are able to identify which light is from the signal arms 72a–c and which is from the reference arms 70a–c. Each of the detectors 80a–c produces a probe signal, which is proportional to the intensity of the light received from the respective signal arms 72a–c, and a reference signal, which is proportional to the intensity of the light received from the respective reference arms 70a–c. Each pair of probe and reference signals originating from the same light source (for example, one of the group of light sources 10a–c ) are compared to each other to determine the atomic absorption of the particular atomic species having the same wavelength as the corresponding light source. The comparison step can be done in the detectors 80a–c or in a separate comparator. The probe signal generated by detector 80a is compared to the reference signal generated by detector 80a to determine the atomic absorption of the Aluminum species. Likewise, the probe signal generated by detector 80b is compared to the reference signal generated by detector 80b to determine the atomic absorption of the Gallium species. Lastly, for example purposes only, the probe signal generated by the detector 80c is compared to the reference signal generated by detector 80c to determine the atomic absorption of the Indium species.

In an alternative embodiment there are a total of six detectors. One detector is connected to each of the optic fibers 88a–c in the signal arms 72a–c and one detector is connected to each optic fiber 74a–c in the reference arms 70a–c.

The second embodiment also must be normalized and calibrated. The molecular beam shutters 104a–b and optical shutters 105a–d are the same as the molecular beam shutters 66a–b and the optical shutters 67a–d respectively.

Figure 5:
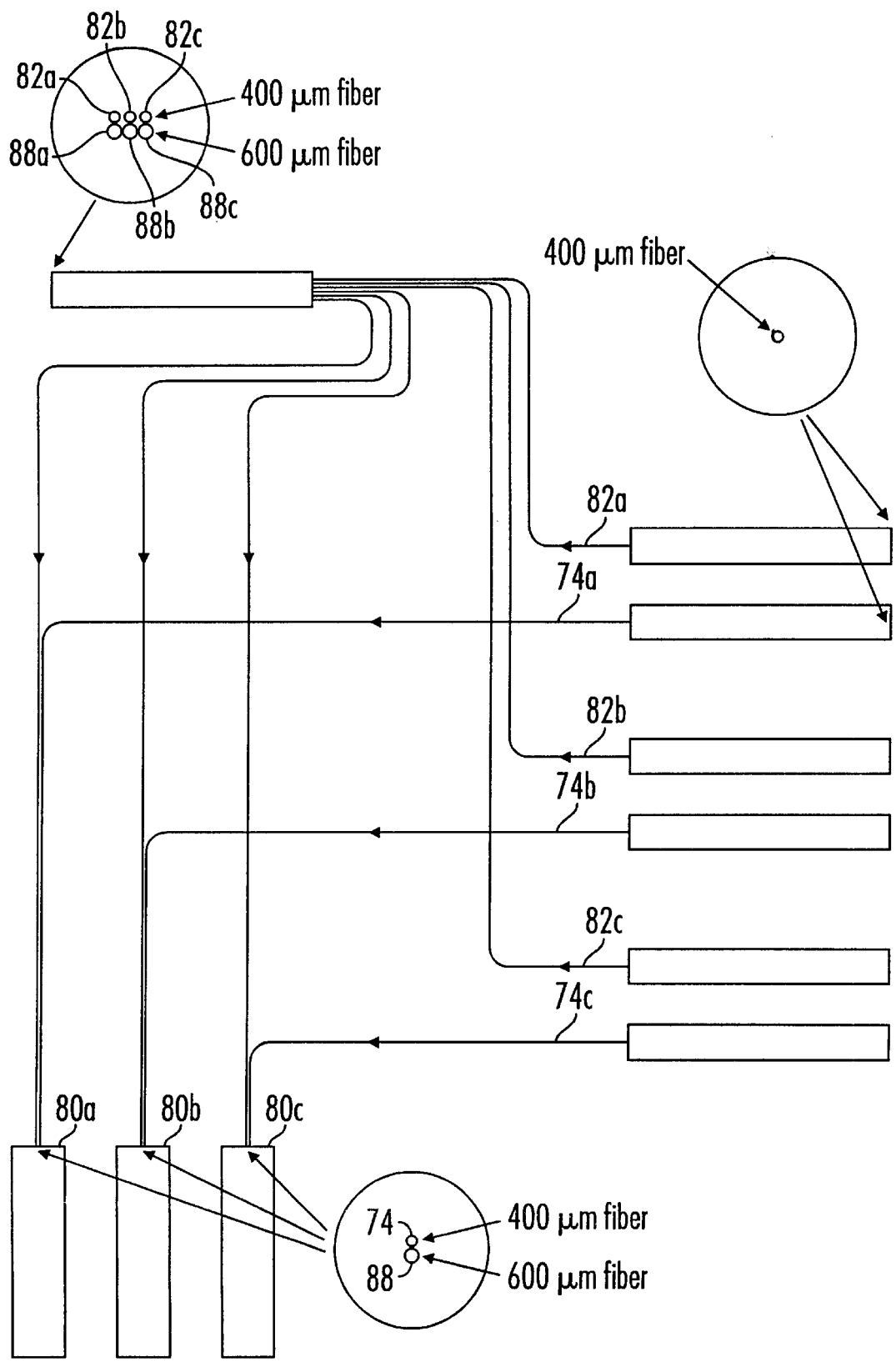
FIG. 5 is a view of the fiber optics in the second embodiment.

FIG. 5 is a view of the fiber optics in the second embodiment of the present invention. The optic fibers 82a–c leading to the vacuum chamber and the optic fibers 74a–c of the reference arms 70a–c (which lead to the detectors 80a–c) are shown in cross section to have a diameter of 400 micrometers, NA=0.16 and a cladding diameter of 0.250", for example. The collection fibers 88a–c are also shown in cross section to have a diameter of 600 micrometers with NA=0.39. The collection fibers 88a–c lie adjacent and underneath optic fibers 82a–c, respectively, as shown in FIG. 5. These six optic fibers are encased in a cladding. In this arrangement of the optic fibers, the light from optic fiber 82a makes a double pass through the region 94 and is then focused into the collection fiber 88a. The light from optic fiber 82b is collected in collection fiber 88b and the light from optic fiber 82c is collected in collection fiber 88c. As can be seen in the cross section of the optic fibers entering the detectors 80a–c, the optic fibers 74a–c are joined into one cladding with their corresponding collection fiber 88a–c which then enter the corresponding detector 80a–c.

Figure 6:
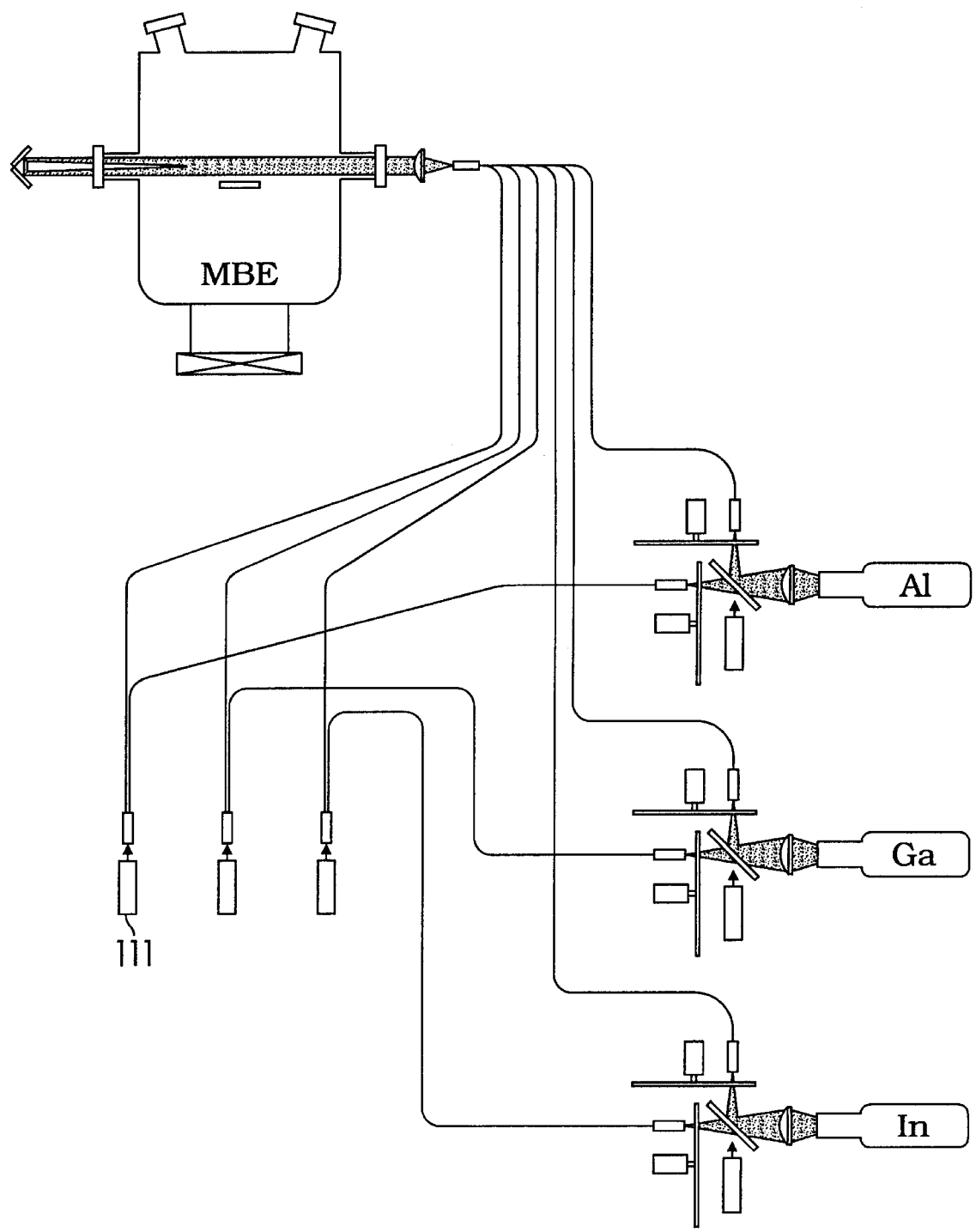
FIG. 6 is a schematic diagram of the second embodiment including the alignment light sources.

FIG. 6 shows the alignment setup for the second embodiment. The alignment of the second embodiment follows the same concepts as for the first embodiment as described above. Three alignment light sources 111 are injected at each of the beam splitters 30a–c, and each of the detectors 80a–c are replaced by an alignment light source. Once the optics are properly aligned, the detectors 80a–c are reconnected back to the fiber optic network.

Figure 7A:
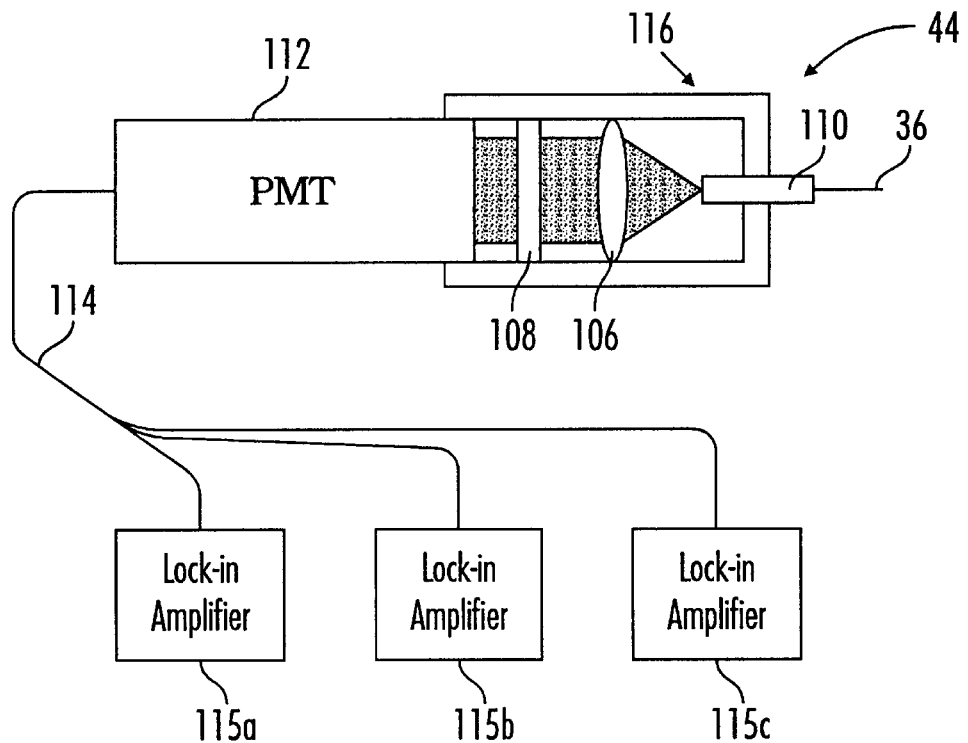
FIG. 7A shows a detector of the first embodiment of the present invention.

FIG. 7A shows the detector 44 used in the first embodiment of the present invention. This discussion also applies to the detector 65 which is identical to the detector 44. At the entrance of the detector 44, the light exits optic fiber 36 via optic fiber end 110 at the focal point of the lens 106. The light passes through the lens 106 and to a PMT 112. Directly in front of each PMT 112 is a wide band-pass interference optical filter 108 used to filter out the unwanted radiation and to protect the PMT 112 from saturation. For the first embodiment of the present invention, 350 to 450 nm bandpass filters are used. The light strikes the PMT 112 and the signal corresponding to the intensity of the light striking the PMT 112 exits the PMT 112 through lead 114. The lead 114 carries the signal to the lock-in amplifiers 115a–c. There are three lock-in amplifiers in this illustration corresponding to the monitoring of three atomic species.

Figure 7B:
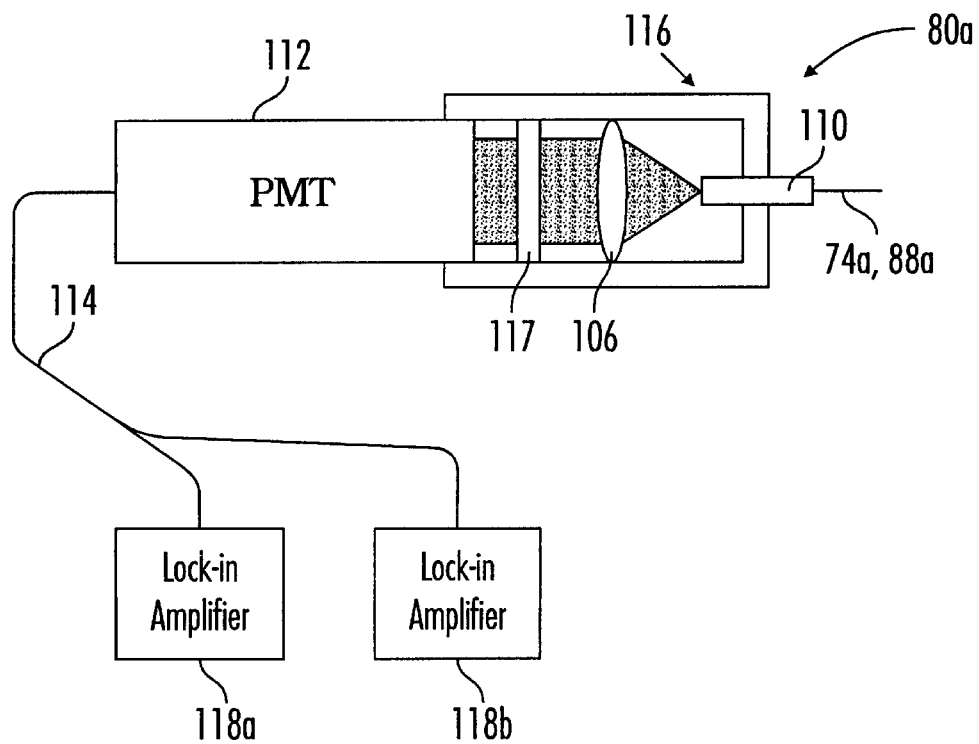
FIG. 7B shows a detector of the second embodiment of the present invention.

FIG. 7B illustrates a detector 80a for the second embodiment of the present invention. Note that the detector 80a could be any of the detectors 80a–c. The detector 80a is different from the detectors 44 and 65 of the first embodiment as shown in FIG. 7A because in the preferred embodiment detector 80a has only two lock-in amplifiers 118a–b regardless of the number of atomic species being monitored. At the entrance of the detector 80a, the optic fiber 74a and the collection fiber 88a are adjacent one another (to create spacial multiplexing) at the focal point of a collimating lens 106 (typically a biconvex lens), at which point such light exits the optic fibers via output fiber end 110. The lens 106 and PMT 112 are the same as in the first embodiment. The filter 117 is a narrow bandpass filter. The two lock-in amplifiers 118a–b are needed to demultiplex the reference signal and probe signal.

Based on experimental results, a typical RMS noise figure for the first embodiment is 1 part in 1500 of the transmitted signal when averaged over 1 sec of data. The accuracy improves with longer averaging time. Without port coating, signal drift of our current test system is no more than 1 part in 1000 over one hour. However, during operation with As coating of the optical ports, the transmission signal drifts on the order of 1% per hour. By incorporating the use of heated optical ports and operating them above 200° C., signal drift due to As coating can be eliminated.

Figure 8:
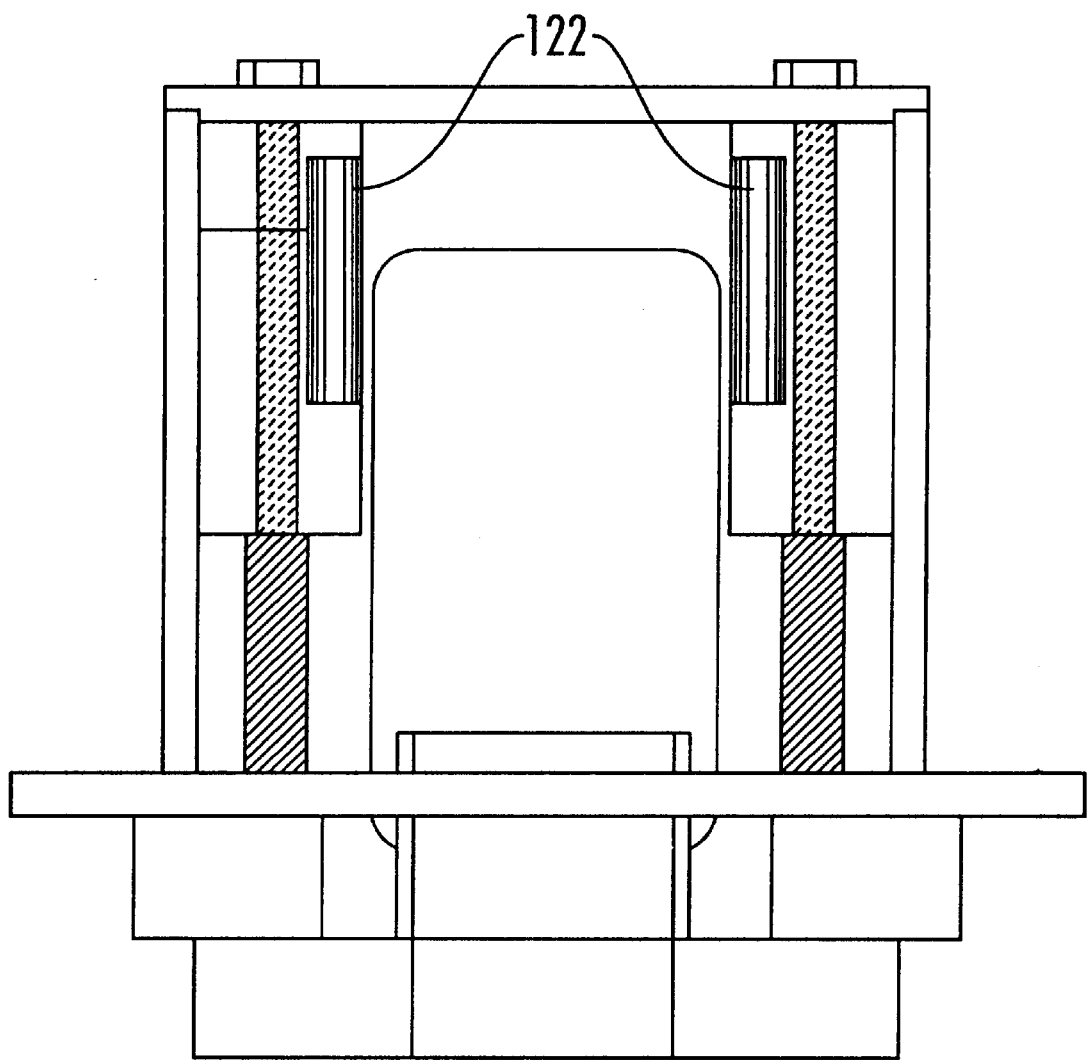
FIG. 8 shows a perspective view of the heated port of the present invention.

FIG. 8 shows a perspective view of the heated port of the present invention. For each port, a thermal couple 120, placed between the side of the port and the cylindrical heating element 122, along with a standard PID controller (not shown), is used for temperature regulation. The heated ports are continuously operated in the range of 300 to 450 degrees C. During several months of operation, arsenic coating of heated ports was virtually eliminated. The optic fiber 40 (in the first embodiment) or optic fibers 82a–c and collection fibers 88a–c (in the second embodiment), the collimating lens 106 and a pair of flat mirrors (the retroreflector 62 or 103) are all enclosed along with the heated ports within a light tight housing 116. An additional benefit of the heated port is that the above mentioned components that are within the port are all kept at a constant temperature throughout the day for improved stability.

Experiments with the first embodiment have been performed to compare the atomic absorption intensity of the molecular beam (in an MBE system) to the growth rate measured by Reflection High Energy Electron Diffraction (RHEED) oscillations. The results are included here for a better understanding of the present invention.

Figure 9:
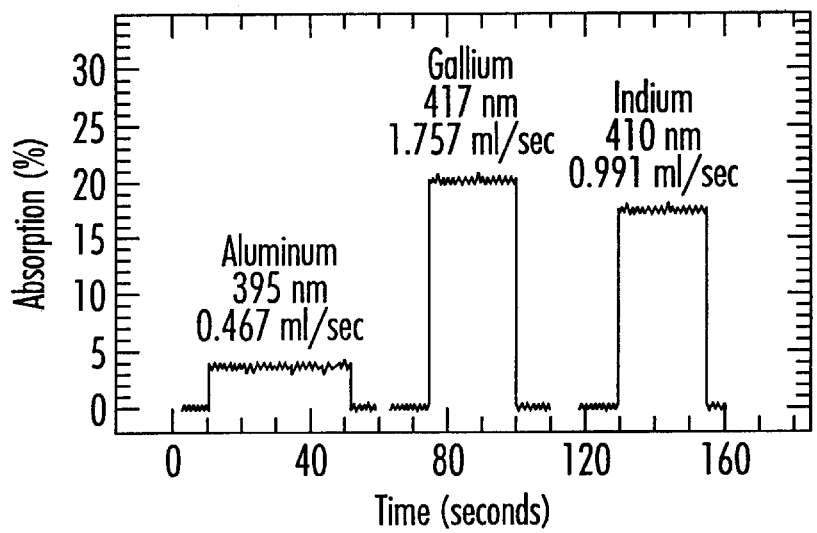
FIG. 9 is a graph of absorption signals for three different sources.

In the experimental arrangement, one pair of 5° glancing-angle optical ports on an MBE system was modified for use with the Optical-based Flux Monitor (OFM). The optical ports on the MBE system are 1.51" in diameter and approximately 3 ft. apart. Both ports have UHV mechanical shutters. The light in the signal arm passes through the vacuum chamber in front of the substrate and is then reflected back by a pair of flat mirrors (retroreflector 62). The returning light is collected by the collection fiber 64 (1.5 mm core diameter) which carries the light to the detector 65. FIG. 9 shows the absorption of Al, Ga, and In at the indicated growth rates. The growth rates were determined by observing RHEED oscillations. The monitored wavelengths are as indicated. Each trace corresponds to the source shutter operations of close/open/close. The absolute growth rates were calibrated by RHEED oscillations. For data acquisition, a Macintosh Quadra 840AV computer equipped with a multi-channel 16 bit Analog to Digital Converter board was used.

Because of offsets in the lock-in amplifiers and also due to stray light in the monitoring system it is preferred to normalize the measured signals. The effect of each light source intensity drift is normalized by dividing each probe signal by the reference signal. The reference signal is the signal measured in the reference arm when the light in the reference arm is not blocked (by the optical shutters 67a–c, for example) minus the signal measured in the reference arm when the light in the reference arm is blocked. For simplicity the discussion of normalization uses the reference numerals from the first embodiment. However, this is not meant to be limiting as these steps are also applicable to the second embodiment.

The comparison of the probe signal to the reference signal involves the following steps. First, the optical shutter 67d is closed and the intensity of the light in the signal arm is measured. This measured intensity will be referred to herein as the light blocked signal intensity. Next, the shutter 67d is opened and the shutter 66a or 66b, or both, whichever corresponds to the atomic species to be measured, is closed. The blocking of the molecular beam flux is typically achieved by valves or shutters. The measured intensity in the signal arm under these conditions is referred to herein as the flux blocked signal intensity. Lastly, the shutter 67d is opened and the shutter 66a or 66b, or both, whichever corresponds to the atomic species to be measured, is opened. The measured intensity in the signal arm under these conditions is referred to herein as the nonblocked signal intensity.

The light blocked signal intensity is divided by the reference signal resulting in the normalized probe intensity offset, R. The flux blocked signal intensity is divided by the reference signal and the normalized probe intensity offset, R, is subtracted off resulting in the transmitted probe intensity, $T_o$. Lastly, the nonblocked signal intensity is divided by the reference signal resulting in the normalized probe intensity signal, $R+T_o-A$.

Once the normalized probe intensity offset, transmitted probe intensity and normalized probe intensity signal are found, then the normalized absorption is calculated. The normalized absorption which is the useful parameter is denoted as $\gamma \equiv A/T_o$.

The normalized absorption is most useful because of its relationship to the growth rate of the epitaxial layers. Under the growth condition that re-evaporation of the monitored atomic species is negligible, the growth rate is a one-to-one monotonically increasing function of absorption. Fortunately, re-evaporation is not a problem for our growth condition—sufficiently low substrate temperature with As over-pressure and growth rate limited by the incident flux of the group III elements.

Since OFM measures the atomic absorption of the material in the region 54 being deposited and not the growth rates directly, the OFM signals must be calibrated using other techniques. For MBE, RHEED is the most practical choice. During calibration, the sample is not rotated. The calibrating RHEED electron beam is positioned at the center of the sample (substrate) where the monitored growth rate should be independent of sample rotation. Typically, sample rotation is preferred during growth because it improves epitaxial uniformity across the wafer. The disadvantage of rotation is that many monitoring techniques which directly probe the substrate such as RHEED, pyrometric interferometry, reflection and transmission spectroscopy, and ellipsometry become more difficult to implement. To partially circumvent this problem, many investigators have synchronized their data acquisition to sample rotation or averaged over several rotation periods. Therefore, the measurement speed for these other techniques is restricted by the period of sample rotation, while an OFM is free from this limitation.

Figure 10:
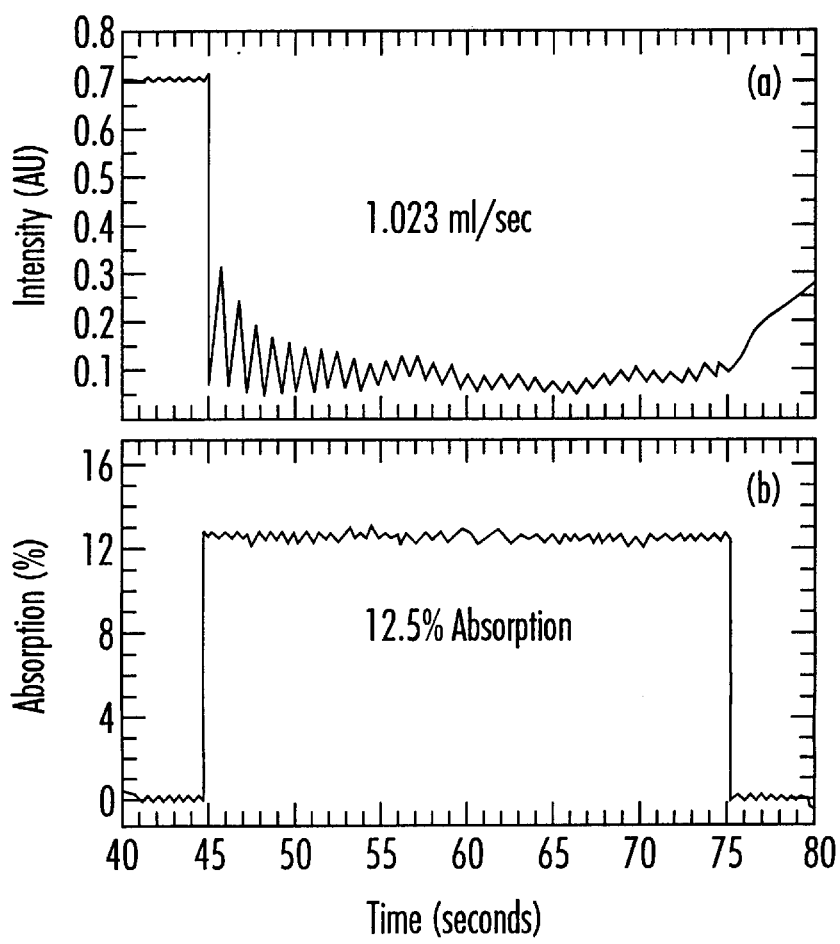
FIG. 10 is a graph showing the RHEED and the Ga absorption data for GaAs calibration.
Figure 11:
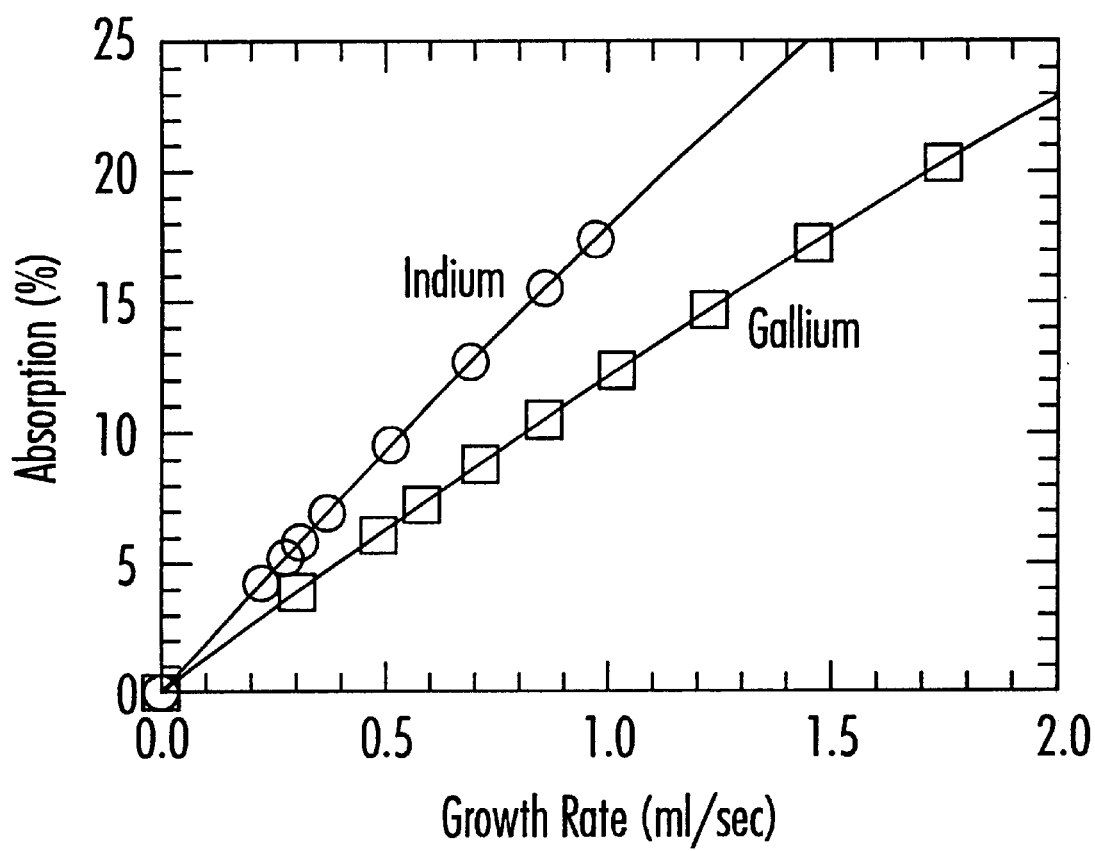

To calibrate the OFM, the atomic absorption of the material being deposited and RHEED oscillation signals are measured simultaneously. FIG. 10 shows the RHEED and the Ga absorption data for GaAs calibration. The growth rate (1.023 monolayers/second) is determined from the period of RHEED oscillations. The absorption and RHEED data were taken simultaneously. Unlike the OFM signal, RHEED oscillations decay away over time; therefore, they become ineffective for monitoring growth of thicker layers. In FIG. 11, atomic absorption signals as a function of growth rate for Ga and In are shown. The substrate temperatures were 620 degrees C. and 520 degrees C. for the GaAs and InAs respectively. RHEED calibrations were measured on GaAs and InAs substrates, respectively. The lines through the data are the Modified Beer's Law fits of the form:

$$\gamma = 1 - exp[-(\alpha+\beta r)r]$$

where r is the growth rate, and $\alpha$ and $\beta$ are the two fit parameters for the growth rate dependent absorption coefficient, $(\alpha+\beta r)$. The growth rate dependence of the absorption coefficient is likely due to a) the differences between the linewidth of atomic emission for an HCL and the absorption linewidth of the beam flux, and b) growth rate dependent absorption coefficient not being a constant because the beam flux velocity changes with changing cell temperature. The discrepancy between the fit and the data is about 0.5%. However, by assuming a constant absorption coefficient ($\beta=0$) for the fit, the discrepancy between the fit and the data increases significantly to about 2.5%.

The system developed is a compact multi-channel optical-based flux monitoring system based on atomic absorption. RHEED oscillations were used to calibrate the OFM so the system can accurately monitor in real-time the individual growth rates of Al, Ga, and In.

While the present invention has been described in connection with the preferred embodiment thereof, it will be understood that many modifications will be readily apparent to those of ordinary skill in the art, and this application is intended to cover any adaptations or variations thereof. Therefore, it is manifestly intended that this invention be limited only by the claims and the equivalents thereof.

What is claimed is:

1. A method of monitoring atomic absorption of a plurality of atomic species during epitaxial growth on a substrate comprising the steps of:

energizing at least two light sources so that light is emitted therefrom, each light source emitting a distinct wavelength corresponding to an atomic absorption transition for each corresponding atomic specie being monitored and modulated at a different modulation frequency;

combining the light from the light sources;

splitting the combined light into a reference arm and a signal arm;

transmitting the light in the signal arm along an optical path through a flux of material being deposited on a substrate in a vacuum chamber; and comparing each distinct wavelength emitted from each light source in the reference arm to the corresponding distinct wavelength corresponding to an atomic absorption transition for each corresponding atomic specie being monitored in the signal arm after the light in the signal arm has passed through the flux of material being deposited.

2. The method of claim 1, wherein the comparing step includes the steps of converting the light in the reference arm and the signal arm into corresponding pluralities of produced reference signals and produced probe signals, wherein each corresponding produced reference signal and produced probe signal contains a distinct wavelength corresponding to an atomic absorption transition for each corresponding atomic specie being monitored, and comparing the corresponding produced probe signals and produced reference signals to determine atomic absorption.

3. The method of claim 2, wherein the produced reference signals are equal to a signal measured when the light in the reference arm passes through the reference arm minus a signal measured when the light in the reference arm does not pass through the reference arm.

4. The method of claim 3, wherein the comparing step comprises the steps of:

measuring a normalized probe intensity offset, R, by determining the intensity of light in the signal arm when the light in the signal arm does not pass through the signal arm and dividing the determined intensity by the produced reference signal;

measuring a transmitted probe intensity, $T_o$, by determining the intensity of light in the signal arm when the flux of material is blocked from striking the substrate and the light in the signal arm is not blocked from passing through the signal arm and dividing the determined intensity by the produced reference signal and subtracting the normalized probe intensity offset, R;

measuring a normalized probe intensity signal, $R+T_o-A$, where A is a radiation absorbed by the flux, by determining the intensity of light in the signal arm when the flux of material is not blocked from striking the substrate and the light in the signal arm is not blocked from passing through the signal arm and dividing the determined intensity by the reference signal; and calculating a normalized absorption, $\gamma$, using the normalized probe intensity offset, transmitted probe intensity and normalized probe intensity signal according to the relationship $\gamma \equiv A/T_o$.

5. The method of claim 1, wherein the transmitting step further includes the step of retroreflecting the light along the optical path through the vacuum chamber.

6. The method of claim 1 further including the step of combining an alignment beam with the light in the signal arm for alignment of the optical path.

7. A method of monitoring atomic absorption of a plurality of atomic species during epitaxial growth on a substrate comprising the steps of:

energizing a plurality of light sources;

filtering light from the light sources through a plurality of narrow bandpass filters, the output of each narrow bandpass filter being a bandpass output;

modulating the bandpass outputs wherein each bandpass output is chopped at a different frequency;

collecting the bandpass outputs into multiple parallel beams, each parallel beam being contained in a separate optical fiber, the optical fibers comprising an optical bundle;

diverting a portion of each bandpass output, the diverted portion comprising a reference arm and the undiverted portion of each bandpass output comprising a signal arm of each bandpass output;

focusing the undiverted portions of each bandpass output into a first optical fiber, and focusing the diverted portions of each bandpass output into a second optical fiber, wherein a numerical aperture and a diameter of the first optical fiber is substantially equal to a numerical aperture and a diameter of the second optical fiber;

sending the focused undiverted portions of each bandpass output through a vacuum chamber wherein the focused undiverted portions pass through a region between a source and a substrate thereby passing through a flux of material being deposited on the substrate;

producing a plurality of electrical probe signals from the focused undiverted portions of each bandpass output by dividing the focused undiverted portions wherein each of the probe signals corresponds to a bandpass output, wherein the probe signal is a measure of the intensity of the corresponding bandpass output after the bandpass output has passed through the region;

producing a plurality of electrical reference signals from the focused diverted portions of each bandpass output by dividing the focused diverted portions wherein each of the electrical reference signals corresponds to a bandpass output, wherein the electrical reference signal is a measure of the intensity of the plurality of light sources; and comparing each electrical reference signal to the corresponding electrical probe signal to determine the atomic absorption of the plurality of atomic species.

8. The method of claim 7, including the step of modulating the bandpass outputs by a plurality of mechanical choppers.

9. The method of claim 7, wherein the light sources comprise three light sources and wherein the step of collecting the bandpass outputs into multiple parallel beams, which includes the step of using a trifurcating optical fiber bundle.

10. The method of claim 7, wherein the plurality of reference signals are produced by a plurality of phase sensitive lock-in amplifiers.

11. The method of claim 7, wherein the plurality of probe signals are produced by a plurality of phase sensitive lock-in amplifiers.

12. An apparatus for monitoring atomic absorption of a plurality of atomic species during epitaxial growth, comprising:

a plurality of light sources wherein each light source produces a distinct wavelength corresponding to an atomic absorption transition for each corresponding atomic specie being monitored, each light source being modulated at a different frequency;

means for combining the light from the light sources into a combined beam in a single optical fiber;

a beam splitter for splitting the combined beam into a reference arm and a signal arm;

a vacuum chamber for performing a deposition of material on a substrate, the chamber comprising a source and a first port, wherein the signal arm is aligned with the first port and the light in the signal arm passes through the first port and through a region between the source and the substrate;

a first detector for receiving the light in the reference arm, and for producing a plurality of reference signals corresponding to the distinct wavelength of each of the light sources in response thereto; a second detector for receiving the light in the signal arm after the light in the signal arm passes through a flux of material in the region between the source and the substrate, and for producing a plurality of probe signals corresponding to the distinct wavelength of each of the light sources in response thereto; and means for comparing each probe signal to the corresponding reference signal for each wavelength of light to determine the atomic absorption of the plurality of atomic species.

13. The apparatus of claim 12, wherein the reference signals are equal to a signal measured when the light in the reference arm passes through the reference arm minus a signal measured when the light in the reference arm does not pass through the reference arm.

14. The apparatus of claim 13, wherein the means for comparing comprises:

means for measuring a normalized probe intensity offset, R, by determining the intensity of light in the signal arm when the light in the signal arm does not pass through the signal arm and dividing the determined intensity by the reference signal;

means for measuring a transmitted probe intensity, $T_o$, by determining the intensity of light in the signal arm when the flux of material is blocked from striking the substrate and the light in the signal arm is not blocked from passing through the signal arm and dividing the determined intensity by the reference signal and subtracting the normalized probe intensity offset, R;

means for measuring a normalized probe intensity signal, $R+T_o-A$, where A is a radiation absorbed by the flux, by determining the intensity of light in the signal arm when the flux of material is not blocked from striking the substrate and the light in the signal arm is not blocked from passing through the signal arm and dividing the determined intensity by the reference signal; and means for calculating a normalized absorption, $\gamma$, using the normalized probe intensity offset, transmitted probe intensity and normalized probe intensity signal according to the relationship $\gamma \equiv A/T_o$.

15. The apparatus of claim 12, wherein the light sources comprise three light sources.

16. The apparatus of claim 15, wherein the means for combining comprises a trifurcating optical fiber bundle.

17. The apparatus of claim 12, wherein the vacuum chamber further comprises a second port, wherein the light from the signal arm enters the vacuum chamber via the first port and exits the vacuum chamber via the second port.

18. The apparatus of claim 17, further including a retroreflector positioned outside the second port of the vacuum chamber, wherein the light from the signal arm, after exiting the vacuum chamber through the second port, is retroreflected into the vacuum chamber via the second port and then exits the vacuum chamber via the first port, thereby completing two passes through the region between the source and the substrate.

19. The apparatus of claim 17, wherein the first and second ports each comprise a heater for maintaining a substantially constant temperature of the respective first and second ports to substantially eliminate coating of the respective first and second ports during the epitaxial process.

20. The apparatus of claim 12, further including a retroreflector attached to the inside of the chamber, wherein the light from the signal arm is retroreflected through the vacuum chamber exiting through the first port, thereby completing two passes through the region between the source and the substrate.

21. The apparatus of claim 20, wherein the retroreflector further comprises a heater for maintaining a substantially constant temperature of the retroreflector to substantially eliminate coating of the retroreflector during the epitaxial process.

22. The apparatus of claim 12, wherein the first detector comprises:

a collection lens wherein the light entering the detector passes through the collection lens;

a filter aligned with the collection lens such that the light entering the detector and passing through the collection lens passes into the filter;

a photomultiplier tube aligned with the filter such that the light exiting the filter strikes the photomultiplier tube, the photomultiplier tube having an electrical output; and a plurality of lock-in amplifiers electrically connected to the output of the photomultiplier tube.

23. The apparatus of claim 12, wherein the second detector comprises:

a collection lens wherein the light entering the detector passes through the collection lens;

a filter aligned with the collection lens such that the light entering the detector and passing through the collection lens passes into the filter;

a photomultiplier tube aligned with the filter such that the light exiting the filter strikes the photomultiplier tube, the photomultiplier tube having an electrical output; and a plurality of lock-in amplifiers electrically connected to the output of the photomultiplier tube.

24. The apparatus of claim 12, wherein the light sources are selected from a group consisting of hollow cathode lamps, laser diodes and laser systems.

25. The apparatus of claim 12, further comprising an alignment light source injecting an alignment light into the reference arm and the signal arm such that the alignment light is combined with the combined beam for aligning the signal arm to the vacuum chamber.

26. A method of monitoring atomic absorption of a plurality of atomic species during epitaxial growth on a substrate, comprising the steps of:

energizing at least two light sources to emit light beams of different wavelengths wherein each light source is modulated at a different frequency;

splitting the light beam from each light source into a reference arm and a signal arm, such that there are at least two reference arms and at least two signal arms and each reference arm has a corresponding signal arm;

positionally and angularly overlapping the light beams from the signal arms to share at least a portion of an optical path that passes through a flux of material in a vacuum chamber, the light beams being positioned to emerge from the vacuum chamber separately;

collecting each light beam separately after the light beams have emerged from the vacuum chamber; and comparing the light beam from each reference arm to the corresponding light beam that has emerged from the vacuum chamber to determine atomic absorption.

27. The method of claim 26, wherein the comparing step includes the steps of converting the light beam in the reference arm and the signal arm into a plurality of converted reference signals and a corresponding plurality of converted probe signals, respectively, and comparing the converted probe signals to the corresponding converted reference signals.

28. The method of claim 27, wherein the converted reference signals produced are equal to a signal measured when the light in the reference arm passes through the reference arm minus a signal measured when the light in the reference arm does not pass through the reference arm.

29. The method of claim 28, wherein the comparing step comprises the steps of:

measuring a normalized probe intensity offset, R, by determining the intensity of light in the signal arm when the light in the signal arm does not pass through the signal arm and dividing the determined intensity by the converted reference signal;

measuring a transmitted probe intensity, $T_o$, by determining the intensity of light in the signal arm when the flux of material is blocked from striking the substrate and the light in the signal arm is not blocked from passing through the signal arm and dividing the determined intensity by the converted reference signal and subtracting the normalized probe intensity offset, R;

measuring a normalized probe intensity signal, $R+T_o-A$, where A is the radiation absorbed by the flux, by determining the intensity of light in the signal arm when the flux of material is not blocked from striking the substrate and the light in the signal arm is not blocked from passing through the signal arm and dividing the determined intensity by the converted reference signal; and calculating a normalized absorption, $\gamma$, using the normalized probe intensity offset, transmitted probe intensity and normalized probe intensity signal according to the relationship $\gamma \equiv A/T_o$.

30. The method of claim 26, further comprising the step of retroreflecting the light in the signal arm through the vacuum chamber.

31. The method of claim 26, further comprising the step of combining an alignment beam with the light in the signal arm for alignment of the signal arm with the optical path through the vacuum chamber.

32. The method of claim 26, wherein the light beams in the signal arm are transmitted through a first plurality of optic fibers.

33. The method of claim 32, wherein the step of positionally and angularly overlapping the light beams from the signal arms comprises the steps of placing the optic fibers of the signal arm adjacent to each other and focusing the light beams in the signal arm through a lens such that the lens focuses the light beams into the adjacent optic fibers.

34. The method of claim 33, wherein the step of collecting each light beam separately after the light beams have emerged from the vacuum chamber comprises the step of capturing the focused light beams in a second plurality of optic fibers such that the light beams are divided into the second plurality of optic fibers.

35. The method of claim 34, wherein the second plurality of optic fibers has a numerical aperture greater than the numerical aperture of the first plurality of optic fibers.

36. A method of monitoring atomic absorption of a plurality of atomic species during epitaxial growth on a substrate, comprising the steps of:

energizing a plurality of light sources to generate light therefrom, each light source generating a distinct wavelength corresponding to an atomic absorption transition for each corresponding atomic specie being monitored;

splitting the light from the light sources into a plurality of reference arms and a plurality of signal arms, wherein there is one reference arm and one signal arm corresponding to each light source;

modulating the light in each of the reference arms and each of the signal arms by chopping the light in each of the arms individually at a distinct chopper frequency with respect to each of the other arms;

producing a plurality of reference signals corresponding to the light in each reference arm wherein each reference signal is proportional to the intensity of the light from a reference arm;

sending the light from the signal arm through the vacuum chamber wherein the light from the signal arm passes through a region between a source and a substrate thereby passing through a flux of material being deposited on the substrate;

capturing the light from the signal arm in an optic fiber;

producing a plurality of probe signals from the light in each signal arm wherein each probe signal is proportional to the intensity of light in a signal arm; and comparing the reference signal to the probe signal for each light source to determine the atomic absorption of the plurality of atomic species.

37. The method of claim 36, wherein the modulating steps are performed by a plurality of mechanical choppers.

38. The method of claim 36, wherein the step of producing the probe signals comprises the step of demultiplexing the probe signals with a plurality of phase sensitive lock-in amplifiers.

39. An apparatus for monitoring atomic absorption of a plurality of atomic species during epitaxial growth on a substrate, comprising:

a plurality of light sources emitting light, wherein each light source produces a distinct wavelength corresponding to an atomic absorption transition for each corresponding atomic specie being monitored, each light source being modulated at a different frequency;

a beam splitter for splitting the light into a plurality of reference arms and a plurality of signal arms, wherein there is one reference arm and one signal arm corresponding to each light source;

a vacuum chamber for performing a deposition of material on the substrate, the chamber comprising a source of growth material and at least a first port wherein the plurality of signal arms are aligned with the first port and the light in the signal arms pass through the first port and through a region between the source of growth material and the substrate, said substrate being contained within the vacuum chamber;

a plurality of detectors for receiving the light from the reference arms and the signal arms, and producing a plurality of reference signals and a plurality of probe signals in response thereto; and means for comparing each of the probe signals for one light source to the reference signals for the same light source to determine the atomic absorption of the atomic species, wherein each reference signal corresponds to the intensity of light in a reference arm and each probe signal corresponds to the intensity of light in a signal arm.

40. The method of claim 39, wherein the reference signals produced are equal to a signal measured when the light in the reference arm passes through the reference arm minus a signal measured when the light in the reference arm does not pass through the reference arm.

41. The apparatus of claim 40, wherein the means for comparing comprises:

means for measuring a normalized probe intensity offset, R, by determining the intensity of light in the signal arm when the light in the signal arm passes through the signal arm and dividing the determined intensity by the reference signal;

means for measuring a transmitted probe intensity, $T_o$, by determining the intensity of light in the signal arm when the flux of material is blocked from striking the substrate and the light in the signal arm is not blocked from passing through the signal arm and dividing the determined intensity by the reference signal and subtracting the normalized probe intensity offset, R;

means for measuring a normalized probe intensity signal, $R+T_o-A$, where A is a radiation absorbed by the flux, by determining the intensity of light in the signal arm when the flux of material is not blocked from striking the substrate and the light in the signal arm is not blocked from passing through the signal arm and dividing the determined intensity by the reference signal; and means for calculating a normalized absorption, γ, using the normalized probe intensity offset, transmitted probe intensity and normalized probe intensity signal according to the relationship $\gamma \equiv A/T_o$.

42. The apparatus of claim 39, wherein the light sources comprise three light sources.

43. The apparatus of claim 39, wherein the vacuum chamber further includes a second port such that the light from the signal arm enters the vacuum chamber through the first port and exits the vacuum chamber through the second port.

44. The apparatus of claim 43, further including a retroreflector positioned outside the second port of the vacuum chamber wherein the light from the signal arm, after exiting the vacuum chamber via the second port, is retroreflected into the vacuum chamber via the second port and then exits the vacuum chamber via the first port, thereby completing two passes through the region between the source and the substrate.

45. The apparatus of claim 43, wherein the first and second ports each include a heater for maintaining a substantially constant temperature of the respective first and second ports to substantially eliminate coating of the respective first and second ports during the epitaxial process.

46. The apparatus of claim 45, wherein the retroreflector further comprises a heater for maintaining a substantially constant temperature of the retroreflector to substantially eliminate coating of the retroreflector during the epitaxial process.

47. The apparatus of claim 39, further including a retroreflector attached to the inside of the chamber wherein the light from the signal arm is retroreflected through the vacuum chamber, exiting through the first port, and thereby completing two passes through the region between the source and the substrate.

48. The apparatus of claim 39, wherein each of the plurality of detectors comprises:

a collection lens wherein the light entering the detector passes through the collection lens;

a filter aligned with the collection lens wherein the light entering the detector passes into the filter;

a photomultiplier tube aligned with the filter wherein the light exiting the filter strikes the photomultiplier tube, the photomultiplier tube having an electrical output; and a plurality of lock-in amplifiers electrically connected to the output of the photomultiplier tube.

49. The apparatus of claim 39, wherein the light sources are selected from a group consisting of hollow cathode lamps, laser diodes and laser systems.

50. The apparatus of claim 39, further comprising an alignment light source injecting an alignment light into the signal arm for aligning the signal arm to the vacuum chamber.

51. A device having epitaxial layers manufactured according to the following steps:

placing a substrate in a vacuum chamber;

generating a flux of material from a source;

forming an epitaxial layer on the substrate from the flux of material;

transmitting a plurality of multiplexed light beams through the flux of material, each of the light beams having distinct wavelength corresponding to an atomic absorption transition for each corresponding atomic specie being monitored, and each of the light beams being modulated at a different frequency;

measuring an atomic absorption of the light beams by the flux of material; and adjusting the flux of material in accordance with the measured atomic absorption so that a desired rate of formation of the epitaxial layers is achieved.

52. A method of monitoring the growth of one or more epitaxial layers on a substrate, comprising the steps of:

growing the epitaxial layers on the substrate by generating a flux using a plurality of sources of material;

measuring atomic absorption of the flux by transmitting multiplexed light beams of different wavelengths of light through the flux and modulating the light beams at a different frequency;

measuring a growth rate for the epitaxial layers substantially simultaneously with the measuring of the atomic absorption; and comparing the measured atomic absorption to the measured growth rate to determine a relationship therebetween.

53. The method of claim 52, wherein the measuring growth rate step uses RHEED oscillations.

54. The method of claim 53, wherein the relationship between the measured growth rate and the measured atomic absorption is: $\gamma=1-\exp[-(\alpha+\beta r)r]$ where $\gamma \equiv A/T_o$ is the normalized absorption, A is the radiation absorbed by the flux, $T_o$ is the normalized probe intensity for an atomic species obtained while there is no flux of the atomic species, r is the RHEED growth rate in monolayers per second and $\alpha$ and $\beta$ are fit parameters.

55. The method of claim 52, further comprising the step of controlling the growth of the epitaxial layers using the determined relationship to compute an appropriate amount of atomic species in the flux.

56. The method of claim 52, further comprising the step of controlling the growth of the epitaxial layers using the determined relationship to compute an appropriate composition for the flux.

57. The method of claim 55, wherein the step of controlling the amount of the atomic species in the flux is performed by a removable shutter placed between the source of the flux and the substrate.

58. The method of claim 56, wherein the step of controlling the composition of the flux is performed by a removable shutter placed between the source of the flux and the substrate.

* * * * *